(12) United States Patent
Kornberg et al.

(10) Patent No.: US 11,612,342 B2
(45) Date of Patent: Mar. 28, 2023

(54) EYE-TRACKING COMMUNICATION METHODS AND SYSTEMS

(71) Applicant: EYEFREE ASSISTING COMMUNICATION LTD., Tel Aviv (IL)

(72) Inventors: Itai Kornberg, Ramat Gan (IL); Or Retzkin, Tel Aviv (IL)

(73) Assignee: EYEFREE ASSISTING COMMUNICATION LTD., Tel Aviv (IL)

( * ) Notice: Subject to any disclaimer, the term of this patent is extended or adjusted under 35 U.S.C. 154(b) by 190 days.

(21) Appl. No.: 16/770,592

(22) PCT Filed: Dec. 6, 2018

(86) PCT No.: PCT/IL2018/051335
§ 371 (c)(1),
(2) Date: Jun. 6, 2020

(87) PCT Pub. No.: WO2019/111257
PCT Pub. Date: Jun. 13, 2019

(65) Prior Publication Data
US 2021/0259601 A1    Aug. 26, 2021

Related U.S. Application Data

(60) Provisional application No. 62/595,694, filed on Dec. 7, 2017, provisional application No. 62/642,048, filed
(Continued)

(51) Int. Cl.
*A61B 5/16*     (2006.01)
*A61B 5/369*    (2021.01)
(Continued)

(52) U.S. Cl.
CPC ............ *A61B 5/163* (2017.08); *A61B 5/0205* (2013.01); *A61B 5/369* (2021.01); *A61B 5/7267* (2013.01);
(Continued)

(58) Field of Classification Search
CPC ....... A61B 5/0205; A61B 5/163; A61B 5/369; A61B 5/7267; A61B 5/7405; A61B 5/742;
(Continued)

(56) References Cited

U.S. PATENT DOCUMENTS 4,836,670 A    6/1989  Hutchinson
4,950,069 A    8/1990  Hutchinson
(Continued)

FOREIGN PATENT DOCUMENTS

CN    101893934 A    11/2010
CN    103383596 A    11/2013
(Continued)

*Primary Examiner* — Chun-Nan Lin
(74) *Attorney, Agent, or Firm* — Vorys, Safer, Seymour and Pease LLP; Anthony P. Venturino; Maryellen Feehery Hank (57) ABSTRACT

Provided is a control system that interfaces with an individual through tracking the eyes and/or tracking other physiological signals generated by an individual. The system, is configured to classify the captured eye images into gestures, that emulate a joystick-like control of the computer. These gestures permit the user to operate, for instance a computer or a system with menu items.

9 Claims, 10 Drawing Sheets

Related U.S. Application Data on Mar. 13, 2018, provisional application No. 62/755,680, filed on Nov. 5, 2018.

(51) Int. Cl.

| | |
|---|---|
| *A61B 5/0205* | (2006.01) |
| *A61B 5/00* | (2006.01) |
| *G06F 3/01* | (2006.01) |
| *G06F 3/023* | (2006.01) |

(52) U.S. Cl.
CPC ............ *A61B 5/742* (2013.01); *A61B 5/7405* (2013.01); *A61B 5/746* (2013.01); *G06F 3/013* (2013.01); *G06F 3/015* (2013.01); *G06F 3/0236* (2013.01)

(58) Field of Classification Search
CPC ......... A61B 5/746; G06F 3/013; G06F 3/015; G06F 3/017; G06F 3/0236; G06F 3/0304; G06F 3/0482

See application file for complete search history.

(56) References Cited

U.S. PATENT DOCUMENTS

| | | | |
|---|---|---|---|
| 4,973,149 A | 11/1990 | Hutchinson | |
| 5,912,721 A | 6/1999 | Yamaguchi et al. | |
| 6,421,064 B1 | 7/2002 | Lemelson et al. | |
| 6,456,262 B1 | 9/2002 | Bell | |
| 6,943,754 B2 | 9/2005 | Aughey et al. | |
| 7,766,479 B2 | 8/2010 | Ebisawa | |
| 8,120,577 B2 | 2/2012 | Bouvin et al. | |
| 8,360,578 B2 | 1/2013 | Nummela | |
| 8,593,375 B2 | 11/2013 | Maltz | |
| 8,888,287 B2 | 11/2014 | Yahav | |
| 8,955,973 B2 | 2/2015 | Raffle et al. | |
| 9,171,198 B1 | 10/2015 | Raffle et al. | |
| 9,799,478 B2 | 10/2017 | Kato et al. | |
| 10,976,813 B2 | 4/2021 | Nistico et al. | |
| 2006/0061544 A1 | 3/2006 | Min et al. | |
| 2010/0125816 A1 | 5/2010 | Bezos | |
| 2010/0149073 A1 | 6/2010 | Chaum et al. | |
| 2011/0077548 A1 | 3/2011 | Torch | |
| 2013/0021373 A1 | 1/2013 | Vaught et al. | |
| 2013/0176533 A1* | 7/2013 | Raffle | A61B 3/113 351/209 |
| 2013/0235347 A1 | 9/2013 | Hennessey et al. | |
| 2013/0293488 A1* | 11/2013 | Na | G06F 3/017 345/173 |
| 2013/0307771 A1 | 11/2013 | Parker et al. | |
| 2013/0332827 A1 | 12/2013 | Smith | |
| 2014/0146156 A1* | 5/2014 | Strombom | H04N 7/18 348/78 |
| 2014/0300535 A1 | 10/2014 | Kim et al. | |
| 2014/0368442 A1 | 12/2014 | Vahtola | |
| 2014/0375541 A1 | 12/2014 | Nister et al. | |
| 2015/0288944 A1* | 10/2015 | Nistico | G06F 3/017 345/156 |

FOREIGN PATENT DOCUMENTS

| | | |
|---|---|---|
| JP | 7-49744 A | 2/1995 |
| JP | 10187334 A | 7/1998 |
| JP | 2000-137789 A | 5/2000 |
| JP | 2005-100366 A | 4/2005 |
| JP | 2006-141862 A | 6/2006 |
| JP | 2007-310815 A | 11/2007 |
| JP | 2007-531579 A | 11/2007 |
| JP | 2012-48358 A | 3/2012 |
| KR | 10-2013-0043369 A | 4/2013 |
| KR | 10-2014-0132906 A | 11/2014 |
| WO | 2009093435 A1 | 7/2009 |
| WO | 2015/044851 A2 | 4/2015 |
| WO | 2016/142933 A1 | 9/2016 |

\* cited by examiner

Current menu item – A,B,C,D,E

Up gesture (UG)

> V,W,X,Y,Z

Left gesture (LG)    Center gesture (CG)    Right gesture (RG)

> Delete    Previous menu    Backspace

> F,G,H,I,J

Down gesture (DG)

Predefined gestures sequence (PGS)

> Predefined action
> (e.g. outputting
> emergency alert)

| Number of gestures: | 1 ▾ | Scan time interval | 3 Seconds ▾ | | |
|---|---|---|---|---|---|
| | Left | Right | Up | Down | Blink |
| Start Scan / Select | ◦ | ◦ | ◦ | ◦ | ● |

Figure 10

| Number of gestures: | 2 ▾ | Scan time interval | 3 Seconds ▾ | | |
|---|---|---|---|---|---|
| | Left | Right | Up | Down | Blink |
| Back | ◦ | ● | ◦ | ◦ | ◦ |
| Start Scan / Select | ◦ | ◦ | ◦ | ◦ | ● |

Figure 11

| Number of gestures: | 3 ▾ | | | | |
|---|---|---|---|---|---|
| | Left | Right | Up | Down | Blink |
| Previous | ● | ◦ | ◦ | ◦ | ◦ |
| Next | ◦ | ● | ◦ | ◦ | ◦ |
| Select | ◦ | ◦ | ◦ | ◦ | ● |

Figure 12

|         | Left | Right | Up | Down | Blink |
|---------|------|-------|----|------|-------|
| Previous | O |   |   |   |   |
| Next     |   | O |   |   |   |
| Back     |   |   | O |   |   |
| Select   |   |   |   |   | O |

Figure 13

Number of gestures: 5

|         | Left | Right | Up | Down | Blink |
|---------|------|-------|----|------|-------|
| Previous | O |   |   |   |   |
| Next     |   | O |   |   |   |
| Back     |   |   | O |   |   |
| Select   |   |   |   | O |   |
| Speak    |   |   |   |   | O |

Figure 14

EYE-TRACKING COMMUNICATION METHODS AND SYSTEMS

TECHNOLOGICAL FIELD

The present disclosure concerns a system that permits an individual to operate communication modules or other utilities through tracking any one or combination of an individual's eye or other physiological parameters.

BACKGROUND

System and method for enabling user communication by tracking the eye of a user are known.

WO2016142933 discloses such a system with a selection interface that selectively presents a series of communication options to the user. A light sensor detects light reflected from the eye of the user and provides a correlative signal, which is processed to determine a relative eye orientation with respect to the head of the user. Based on the determined relative eye orientation, a selected communication option is determined and implemented.

GENERAL DESCRIPTION

This disclosure concerns a computerized system that interfaces with an individual through tracking the eyes and/or tracking other physiological signals generated by an individual. In other words, it is a system that comprises a utility having a control unit associated with a camera configured for tracking movement of the eye and/or eyelid and may additionally comprise a utility configured for tracking another physiological parameter. The system, by one embodiment, is configured to classify the captured eye images into gestures, which may be one or more of pupil position or gaze direction, a sequence of directional eye movements, a sequence of blinks of the eyelids, etc. These gestures permit the user to operate, for instance a computer or a system with menu items. In this manner the eye movements can, for example, permit the user to navigate through a menu, move a cursor on a screen through eye movements, select items through fixing the eye in a certain position for a given time period or through a sequence of blinks, navigate through menu items by directing the gaze in accordance with a menu prompt, etc. The system may also classify other physiological data and translate them into commands readable by a computer or configured for operating one or more peripheral devices. For example, The system may permit the user to navigate through a menu by performing a defined eye gesture, or performing a predetermined respiratory pattern, move a cursor on the screen by moving a body part, select items by a respiratory action or based on electrophysiological signals etc. In general, the system of this disclosure permits the user to operate a computer in a manner resembling that of a joystick. By the joystick-like approach of this disclosure the only reference point is a camera capturing images of the eye and there is no need to detect the exact location or position the user is looking at or at a corneal reflection. Also according to this disclosure there is, typically, no need for any calibration procedure using a screen prior to use (and in fact, there is no need to use screen at all in order to communicate using the system).

By some embodiments, a menu is not presented on a screen to the user, and the user's navigation through a menu and items selections are carried out without a screen (based, for instance, on a menu that is predetermined or that was previously introduced or presented to the user).

By some embodiments, a menu is presented on a screen to the user, only during an initial introduction phase, during which for example a feedback, or instructions are provided to the user. Said phase may be any time frame at a scale of minuets, hours, weeks and months.

By some embodiments the gestures permitting the user to operate the computer are general viewing at a defined direction (eye gesture), instead of a gesture in which the user is looking at a particular location (eye gaze). For example, a general left stare may serve as a gesture, even if the user is not focusing his sight at a specific physical or virtual object.

Typically, operation of the system of this disclosure is independent on the lighting conditions.

By some embodiments, gesture classification is based on employing machine learning techniques. Specifically, the machine learning model may be a neural networks model consisting multiple linear transformations layers and subsequent element-wise nonlinearities. The classification may comprise eye characterization of an individual user or across users. By some embodiments the classification estimates the range of eye motion.

By one embodiment, the system permits the individual using the system (herein "user") to navigate through a menu that is presented to the user. The presentation of the menu may be an audible presentation (by means of a loudspeaker, earphones, headphones, implanted audible device, etc.) or a visual presentation (through a display on a screen, a small display in front the individual, etc.). The menu may be hierarchical, meaning that a selection of a menu item may open other, lower hierarchy selectable options. By way example, a higher hierarchy of selectable menu items may permit the user to select one of several letter groups (e.g. one group consisting of the letters A through F, the second group of the letters G through M, etc.) and once selected the user is presented with the ability to select one of another group of letters (e.g. if the first group is selected the user may be giving the option to select between A, B, C or D-F and then if D-F is selected the user is presented with the individual letters for his selection). However, the selection may also be prompt-driven, namely the user may be prompted to move the eye in a certain direction for a certain selection.

By some embodiments, the menu items or portions thereof can be customized for specific needs. This may be achieved locally, e.g. through a user or care-taker interface or may also be achieved remotely, e.g. in a remote server.

The menu items or portions thereof may be proposed to the user by the system or the control unit. The menu items or portions thereof may also be proposed to the user or presented to the user based on inputs received from the environment.

In some embodiments the control unit receives and processes (for example by means of natural language processing) audio data. For example, once the user is asked a question by another person, e.g. a caregiver, the control unit may receive and process the physician speech and propose a response based on a contextual analysis of the speech of the other person. The system of this disclosure is useful for permitting paralyzed individuals that cannot otherwise communicate, to communicate with their environment including care-givers, peripheral devices such an alerting system, an audiovisual system, a computer, etc. One target group of individuals are ALS patient that with the progress in their disease lose any ability for moving limbs or other muscle and the ability to speak and display sounds. The system may also be useful for individuals that have a temporary communication impairment such as patients in an intensive care unit, patients with a temporary or permanent breathing assist, etc.

Provided by an embodiment of this disclosure is a control system for operating a computer, that comprises: a camera configured for continuously capturing images of one or both of a user's eye and eyelid and generating image data representative thereof; and a control unit in data communication with the camera and with the computer. The control unit is operable to receive and process said image data and classify these into gestures that are intended to emulate a joystick-like control of the computer.

The term joystick-like control as described herein refers to gestures classification comprising tracking the position of the pupil area.

The pupil area in the context of this disclosure, is the pupil or any portion thereof, identified as indicative of the pupil.

By some embodiments the position of the pupil area is determined based on a databased comprising image data with labeled gestures. Said image data may be acquired from the user itself or any other user or group of users. By some embodiments the position of the pupil area based on said labeled databased is determined by utilizing machine learning technique, for instance a model considering the likelihood of a given image data to correspond to a particular gesture.

By some embodiments the position of the pupil area may be determined based on its position within a threshold map, wherein a particular position is determined whenever the pupil area touches a border or tangent to a border of the threshold map. For instance, when the pupil area touches the upper border of the threshold map the image data would be classified as an "up" gesture, or when the pupil area is not touching any border of the threshold map the image data would be classified as a "straight" gesture. The threshold map may be derived from a position map, including a region which is within the motion range of the pupil area. By one example, the position map is defined as a rectangle defined by the upper, lower, leftmost and rightmost positions of the pupil area. By some embodiments, the threshold map covers an area limited by a border that is at least 20%, 40%, 60%, 80%, 90%, 95% away from the center of the position map. The threshold map is typically at least 80% away from the center of the position map. The position map may be obtained based on the users' image data or any database comprising image data with or without labeled gestures. Optionally, the position map is within a larger, region of interest (ROI), defined based on anatomical features of the eye or its surrounding.

By some embodiments the system requires the user to perform a straight gesture in between other gestures.

By some embodiments the blink gesture is identified as a region of dark pixels.

By some embodiments a gesture would be classified when the pupil area touches a border or tangent to a border of the threshold map for at least 0.05, 0.1, 0.2, 0.3, 0.4, 0.5, 0.6, 0.7, 0.8, 1, 2, 4, 8, 10 seconds.

By some embodiment the camera is an infrared camera.

In addition, the control unit may be linked with one or more sensors for detecting other physiological measurement and operable to receive and process physiological signals acquired by such device or sensor and classify these into computerized commands.

For example, through movement of the eye (that may be tracked through the position of the pupil relative to the eye socket) and optionally also through eyelids' blinks the user can navigate through selectable options and select them at will. This may include navigation through and selection of menu items, navigation through and selection of hyperlinks, etc. According to one specific and non-limiting embodiment, a directional movement or position of the pupil may direct a cursor in a defined direction, e.g. an upward position of the pupil may move a cursor on a screen in an upwards direction, a right position in the right direction, etc.; or alternatively, rather than only a system defined direction, the direction of movement of such a cursor may be user-defined. As a non-limiting embodiment, the user's blink (or any other gesture or physiological parameter defined by the user) may initiate the camera operation, and subsequent blinks may allow the user to browse through selectable options and select an option by such a blink. According to another example, the menu item may be outputted vocally to the user and when the desired menu item is vocally outputted, the user blinks and selects the desired item. According to another non-limiting embodiments, a user with a limited ability may operate the system using a single gesture, based on his definitions, for instance only "left" gesture. Also, as another exemplary and non-limiting embodiment, the user may be prompted by audio or visual output to select between several options, e.g. "UP" (namely gaze upwards) for one selection, "DOWN" for another, etc. By further exemplary and non-limiting embodiment, the user may be presented (e.g. through an audio read-out) with options and thereby prompting the user to gaze in a specific or non-specific direction, make a series of blinks, close the eyelids for a defined period, etc., when the specific choice is presented. The latter is useful, for example, for a quick selection of letters for writing texts.

By some embodiments any one of the type of gestures, number of gestures, the gestures duration, and the corresponding commands are defined by the user or a caregiver.

By some embodiments a series of 1, 2, 3 or 5 blinks may select a "call for help" item.

By some embodiments a series of up to 10 blinks, within up to 30 seconds selects an item.

By some embodiments closing the eyes for 1, 2, 3, 4, 5, 6, 7, 8, 9, 10, 30 seconds may put the system into rest mode.

The control unit may be configured, according to an embodiment of this disclosure, for (i) receiving and processing said image data to identify at least one of pupil position and eyelid movement and to classify these into gestures, the gestures comprising, for example, one or more of pupil position, sequence of pupil positions, and sequences of eyelid blinks and generating gesture data, and (ii) utilizing the gesture data to operate the computer. By one embodiment the computer that is linked to said control system operates a visual or audio output module. Said output module may permit the user to communicate with other individuals. In some embodiment the audio output module is a bone conduction hearing aid.

In addition the control unit may be configured for and being operable to (i) receiving and processing physiological data and to classify these into commands, the commands comprising, for example, any electrophysiological marker (as recorded for example via Electroencephalography (EEG) device), somatosensory, respiratory, vocal, movement gesture or any combination thereof, and (ii) utilizing the physiological commands to operate the computer. By one embodiment the computer that is linked to said control system operates a visual or audio output module. Said output module may permit the user to communicate with other individuals.

For example, EEG signals may be recorded so that EEG commands initiates a navigation in a time-dependent menu and once the navigation menu reaches the desired menu item, the user may produce an additional EEG commands that selects the menu item. According to another example EEG commands triggers the onset of the system.

Provided by another embodiment of this disclosure is a control unit configured for data communication with at least one sensor for measuring a physiological parameter and with a computer, the control unit being operable to receive and process physiological data acquired by said at least one sensor and classify these into commands, and transmit corresponding commands to the computer to thereby control operation of the computer.

Provided by another embodiment of this disclosure is an eye tracking-based system, comprising a camera, a first output module, and a control unit, typically a computer or processor-containing unit. The camera is operable for continuously capturing images of one or both of the user's eye and eyelid and generating image data representative thereof. The control unit is in data communication with the camera and with the first output module; and is configured for (i) receiving and processing said image data to identify at least one of pupil position and eyelid movement and to classify these into gestures comprising one or more of pupil position, sequence of pupil positions, and sequences of eyelid blinks and generating gesture data, (ii) operating a hierarchical user-selectable menu items to permit the user to navigate through and select menu items by said gestures data, and for (iii) driving the first output module to present the menu items to the user. Optionally the control unit is configured also for data communication with a sensor for measuring a physiological parameter. The control unit may be further configured for (i) receiving and processing physiological data from said sensor and to classify these into commands, (ii) operating a hierarchical user-selectable menu items to permit the user to navigate through and select menu items by said commands, and for (iii) driving the first output module to present the menu items to the user. The first output module is configured for providing the user with one or both of visual or audio presentation of the menu items. In some embodiment the audio presentation module is a bone conduction hearing aid.

Provided by a another embodiment is an eye tracking-based system, which like that of the embodiment discussed in the previous paragraph, comprises a camera, a first output module and a control unit. The camera is operable for continuously capturing images of one or both of the user's eye and eyelid and generating image data representative thereof. The control unit is in data communication with the camera and with the first output module. It comprises a data processor configured and operable to be responsive to the image data received from the camera and process said image data to identify at least one of pupil position and eyelid movement and to classify these into gestures comprising one or more of pupil position, sequence of pupil positions, and sequences of eyelid blinks, and generate gesture data. It also comprises a menu generator module configured and operable to utilize said gesture data to operate a hierarchical, user-selectable menu items. The system further comprises a first actuator module configured to drive the first output module to present menu items to the user via one or both of visual or audio presentation of the menu items to thereby permit the user to navigate through and select menu items.

Optionally, the control unit is in data communication with a sensor for measuring a physiological parameter, it comprises a data processor configured and operable to be responsive to the physiological data received from the sensor and process said physiological data to classify these into commands.

Said gestures may comprise straight, center, right, left, up and down positions of the pupil and blinks. optionally the gestures may comprise sequence of 2 or more eyelid blinks. For example, the right position of the pupil may be classified into "enter" command.

The gesture may selected from any one or combination of eye gestures known in the art, for example the gesture may be a fixation (stationary gaze) or s series of fixations and their durations, gaze points and clusters and distributions thereof.

The system (of any of the above embodiments) may be operable for driving an output module that is configured for outputting an alert signal (typically one or both of an audio and visual signal).

The camera may be mounted on a holder attachable to the user's head. However, the camera may also be mounted on a frame in the vicinity of the user, e.g. a frame of a bed, a frame that carries medical instruments, etc.

Said menu items may be arranged in a hierarchical manner. They may, for example be arranged in a succession hierarchical layers such that a selection of a first menu item permits the user to subsequently select second menu items at a layer subordinate to the first menu item. Each such "layer" may typically comprise up to 5 selectable items—selectable by a center, right, left, up and down positions of the pupil.

In the addition or in the alternative, the menu items may be selected through a prompt-based system; for example, the user may be instructed through a visual or audio prompt to gaze in a certain direction for selection of one menu item, in another direction for a second item, etc.

By some embodiments the menu items are user-definable.

The system may comprise a driver for a second output module. Such a module may be one configured to generate an alert; or one configured to operate peripheral systems, e.g. a virtual assistant, a smart home device, a domestic climate control system, a television set, a music player, a communication device, a wheelchair, a tablet a smartphone, a gaming accessory etc. The system may be configured to operate such a second output module through system-defined or user-defined specific gestures; for example a defined sequence of blinks.

Said physiological measurement or physiological data refers to any signal that may be acquired from the users' body, including any signal acquired from the users' neural, somtatosensory, vocal, and respiratory system as well as motion of selected muscles.

Such sensor for measuring a physiological parameter may be any sensor utility or a measuring device, a microphone, spirometer, galvanic skin response (GSR) device, touch or pressure probes, electrodermal response probe (skin conductance probe), electroencephalography (EEG) device, electroencephalography (ECoG) device, electromyography (EMG), electrooculography (EOG), and electrocardiogram. The data recorded by the sensor would be classified into commands.

Said commands may be any one or combination of a, movement of any body part (for example finger tapping or pressing a response button), respiration pattern, sniffing, vocal output, change in muscle tension, skin conductance, or neural output.

Said neural outputs may, for example, be a measured evoked response potential, or any marker related to the time or frequency of the measured data.

The user of the system of this disclosure may be any needing individual such as an ALS patient, intensive care unit patient, a locked-in patient, a patient without an ability to communicate verbally.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
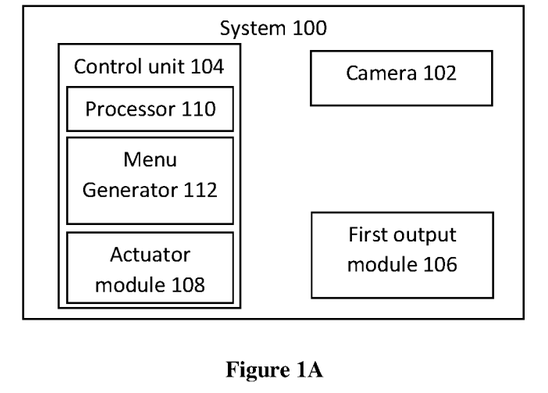
FIG. 1A-1B are schematic block diagrams of a system in accordance with embodiments of this disclosure.
Figure 1B:
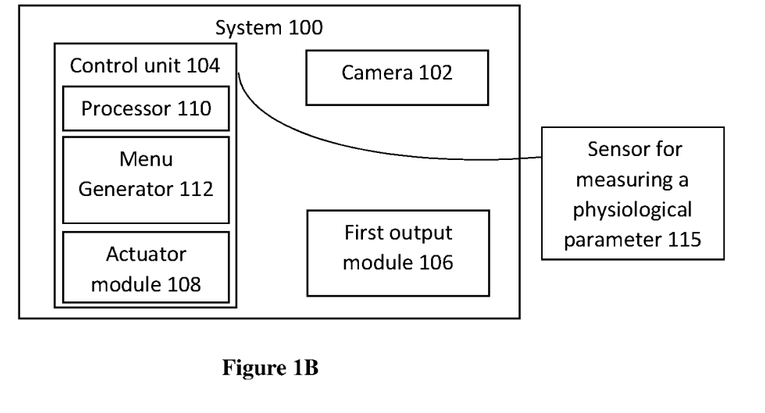

Reference is first made to FIGS. 1A-1B illustrating a schematic block diagram of a system in accordance with an embodiment of this disclosure. The eye tracking-based system 100 comprises a camera 102, mounted on a frame or carried on a holder attached to a user's head. The camera 102 is operable for continuously capturing images of one or both of the user's eye and eyelid and generating image data representative thereof. The system 100 includes a control unit 104 that is in data communication with the camera 102 and with first output module 106, typically through an actuator module 108 that drives the first output module 106. Output module 106 may be a visual display, e.g. digital screen, or an audible device, e.g. speaker, headphones, etc.

Control unit 104 includes also a processor 110 that is configured for receiving and processing image data from the camera 102 and for identifying at least one of pupil position and eyelid movement and to classify these into gestures comprising one or more of pupil position, sequence of pupil positions, and sequences of eyelid blinks and generating gesture data. The processor 110 is also configured for driving the menu generator 112 which, through the action of actuator module 108 drives the presentation of the menu to the user. This permits the user to navigate through and select menu items by said gesture data.

FIG. 1B shows a block diagram of the system of the present disclosure, wherein the system communicates with a sensor for measuring a physiological parameter 115 (for example EEG, Electromyography (EMG), or head motion measurement device). Specifically, the device 115 is in data communication with the control unit 104 which is configured to communicate commands based on the user's detected physiological signal. The physiological signals can be analyzed and translated into commands in the system 100, such as starting the system, initiating navigation process, selecting menu item, etc.

Figure 2:
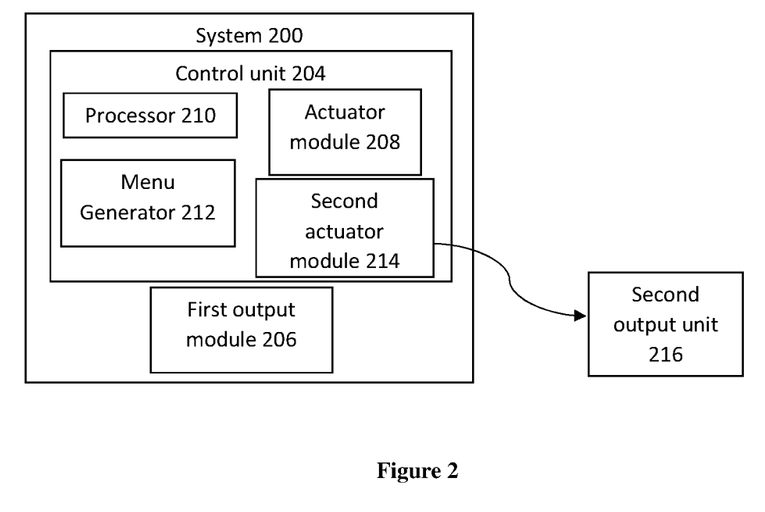
FIG. 2 is a schematic block diagram of a system in accordance with another embodiment of this disclosure.

In FIGS. 2-3 like elements to those of FIGS. 1A-1B were given like reference numerals shifted by 100. For example element 204 in FIG. 2 serves the same function as element 104 in FIGS. 1A-1B. The reader is, thus, referred to the description of FIGS. 1A-1B to understand their meaning and function.

The system of FIG. 2 differs from that of FIGS. 1A-1B in that the former includes also a second actuator module 214 that is operable to drive a second output unit 216 that may be part of the system or an external element such as an alerting device, a display screen, a utility for operating device in the user's vicinity (drapes, music player, lights, etc.). In other words, the second output unit 216 establishes the connection of the system to the environment of the system, by wired (for example infrared) or wireless connections to other devices, connections to a cloud server or connection to communication means with the surrounding of the user. For example, the system can be wirelessly connected, e.g. by Wi-Fi or Bluetooth, to smart home devices that are operable by gestures of a user using the system 200. The system may be configured to drive the second output unit by means of specific defined gestures or through a selectable menu item. Such specific gesture may be pre-defined or user-selectable.

Figure 3A:
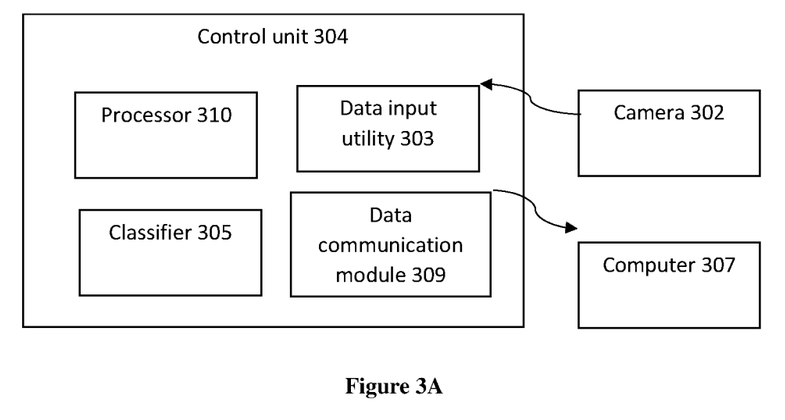
FIG. 3A-3B is a schematic block diagram of a control unit in accordance with an aspect of this disclosure.
Figure 3B:
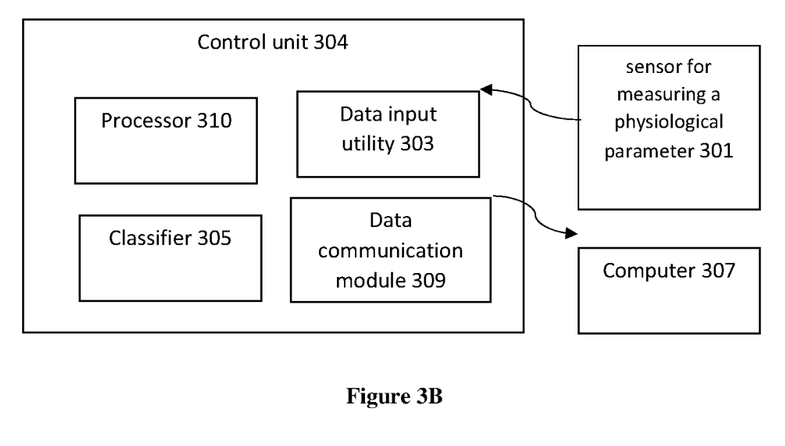

Reference is now being made to FIG. 3 illustrating a schematic block diagram of a control unit in accordance with two aspects of this disclosure. The control unit 304 includes a data input utility 303 that is in data communication with a camera that captures continuous images of the eye. 302 (FIG. 3A) or a with a sensor for measuring a physiological parameter 301 (FIG. 3B) The data received by the data input utility 303 is processed by the processor 310 and processed data is classified by the classifier 305 into gestures. The classified gestures are then being sent to a computer 307 that is in data communication with the control unit by a data communication module 309 to thereby control operation of the computer 307.

Figure 4:
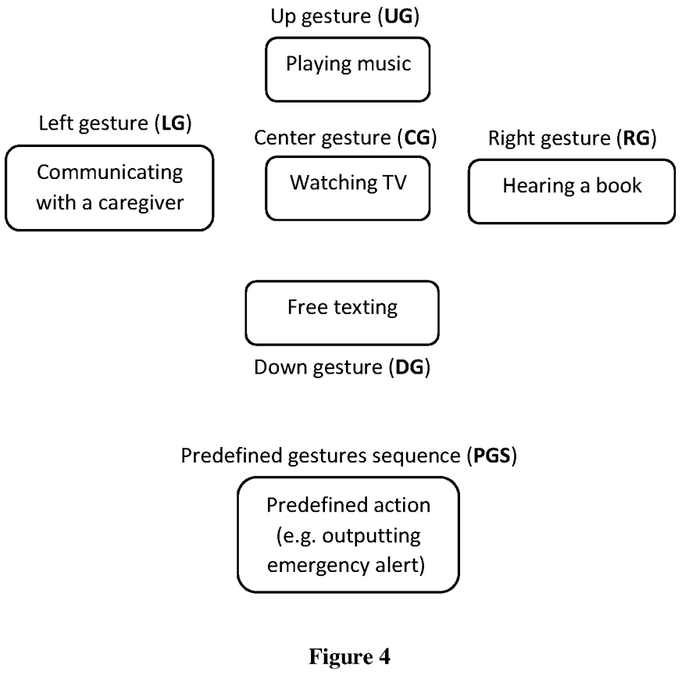
FIG. 4 is a schematic visual depiction of a menu layer in accordance with an embodiment of this disclosure.

Reference is now being made to FIG. 4, which is a schematic visual depiction of a menu layer in accordance with an embodiment of this disclosure. As can be appreciated, the menu layer has several menu items, each one of them is selected by a different gesture. For example, an up gesture UG, namely an up position of the pupil, will be driven a selection of playing music. Accordingly, left gesture LG will be driven communication with a caregiver menu, center gesture CG watching TV, right gesture RG hearing a book and down gesture DG will open free texting menu. Some of the menu items are enabled by wireless connectivity, such as between the TV and the system by Bluetooth or Wi-Fi network, while other menu items are enabled by connectivity to a cloud server such as in the case of hearing a book or playing music. Playing music or hearing a book can be done directly from the cloud server without having the data on a local memory. It should be noted that the data exchange with the cloud may work on both ways, namely data can be downloaded from the cloud to the system and data can be uploaded to the cloud from the system.

At any time and in any layer of the menu, when the user will make a predefined gestures sequence PGS, it will trigger a predefined action such as outputting an emergency alert for a caregiver e.g. by voice alert through a speaker, textual alert to a mobile device, alerting a medical center or any combination thereof. The predefined gestures sequence PGS may be configured according the user's will, for example it can be a sequence of 3 or 4 blinks, a sequence of up gesture UG, down gesture DG, up gesture UG and down gesture DG, or any other desired sequence.

Figure 5:
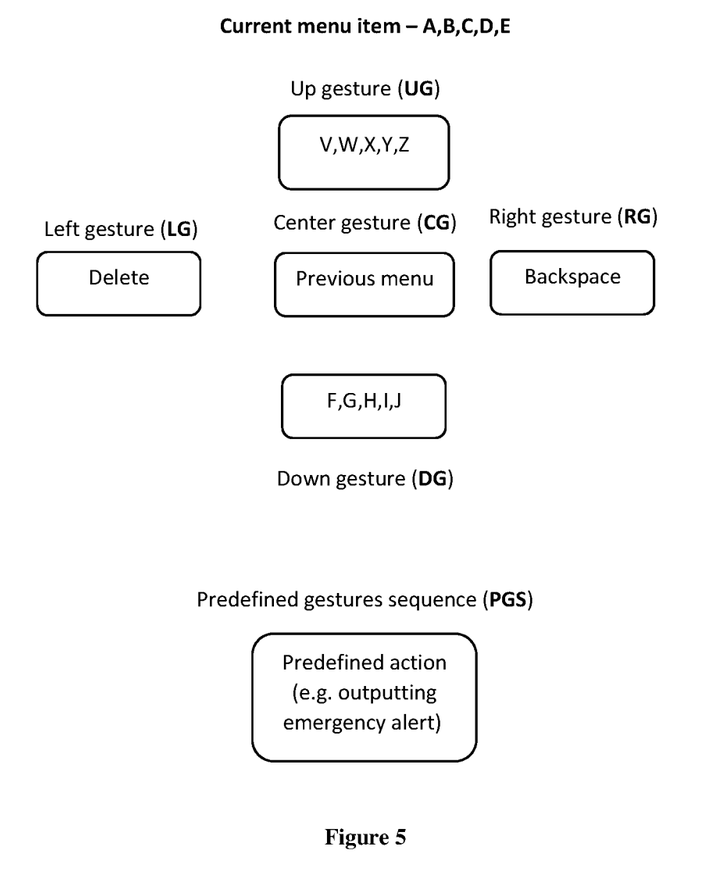
FIGS. 5-6 are schematic visual depictions of a menu layer in accordance with another embodiment of this disclosure.
Figure 6:
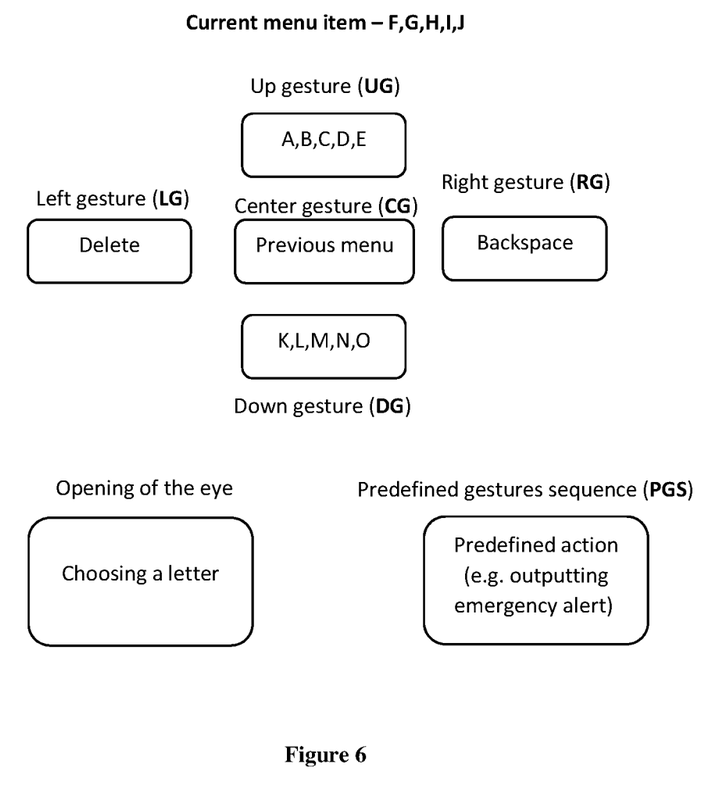
Figure 7:
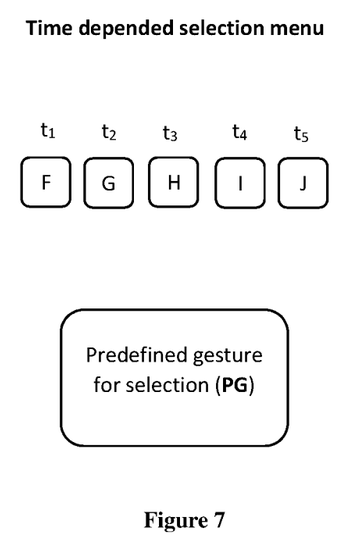
FIG. 7 is a schematic illustration of a time-based prompt menu for selection of items according to an embodiment of this disclosure.

FIGS. 5-7 are schematic visual depictions of a menu layer in accordance with another embodiment of this disclosure, exemplifying a unique method of selection of item menu by a way of free texting. The letters are clustered in groups of letters, e.g. 4, 5 or 6 letters in each group. The user can navigate between the groups and selecting a specific letter in a group by making a specific gesture in the right timing. In FIG. 5 the system is now presenting the group of letters A,B,C,D,E. The user can make an up gesture UG and navigate to the group V,W,X,Y,Z or down gesture DG to navigate the group F,G,H,I,J. Other gestures can be made to trigger other commands such as deleting a letter, using a backspace key or going back to the previous menu, and are brought up only by way of example. It should be noted that these commands can be replaced by any other suitable commands or can be removed. FIG. 6 exemplifies a user selection of down gesture DG in the menu layer of FIG. 5 that triggered a menu item including the group of letters F,G,H,I,J. The system may trigger an automatic output session of the letters in the group, such as announcing the name of each letter, through speakers or headphones, in a time difference from other letters as exemplified in FIG. 7. As can be appreciated, the letter F is announced in a time $t_1$ and the letter G is announced in the time $t_2$ etc. When a specific predefined gesture PG is made, e.g. blinking once or twice, a letter is selected. For example, if the predefined gesture PG is made in time $t_1 < t < t_2$ the letter F will be selected and if the predefined gesture PG is made in time $t_3 < t < t_4$ the letter H will be selected. In another embodiment of the system, the output session of the letters in the group is triggered according to the user request by a predefined gesture PG. That may be of relevance where the subject using the system lacks the capability of performing some of the gestures, such as left, right, up or down gesture. In this scenario, the navigation in the system may initiate by a first predefined gesture $PG_1$ and items menu can be selected by a second predefined gesture $PG_2$, the first and the second predefined gestures may be different or identical. For example, when the system is in the state of FIG. 6, the user may close his eyes to trigger the output session of the letters in the group and when the desired letter is heard, the user opens his eyes for selecting the letter. It should be understood that by making the up or down gestures UG, DG the system will navigate to other groups of letters as can be seen in FIG. 6.

In order to improve classification of the gestures, the system may be trained by a machine/deep learning algorithm. First, the system is received with labeled gestures images (Blink, Center, Up, Down, Right, Left) to gather initial dataset. Then, the system go through a training session with a set of training images. During this training session the system, namely the neural network of the system, learns how to recognize each of the categories in the labeled images. When the present model makes a mistake, it corrects itself and improves. When the training session of the network is over, a testing set of images is received and processed by the system to check the new model of classification. The classification made by the system is compared with the ground-truth labels of the testing set and the number of correct classifications can be computed and values of precision, recall, and f-measure, which are used to quantify the performance of such a network can be obtained.

Figure 8:
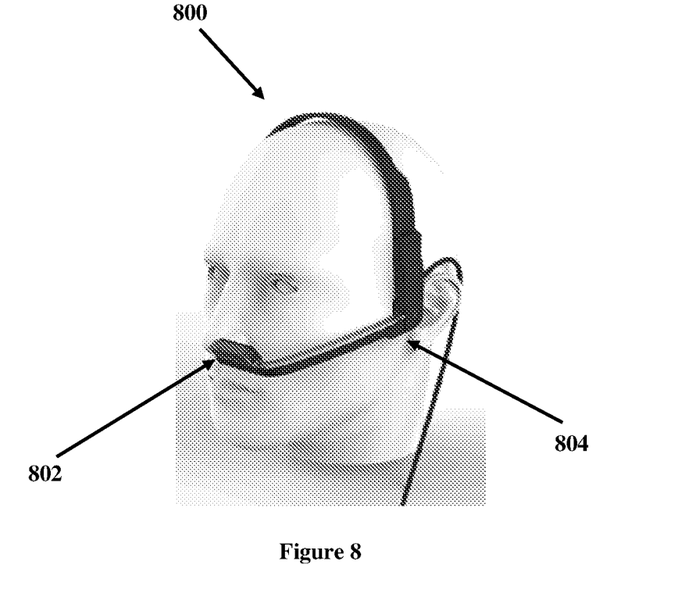
FIG. 8 is a schematic illustration of one embodiment of an eye tracking-based system, comprising a camera, a bone conduction speaker and a control unit.

A schematic illustration of an assistive communication eye tracking-based system is provided by FIG. 8. The system comprise a camera (802) mounted on a lightweight head mount (800, fitted onto the user's head by a family member, a caregiver or the user itself), a bone conduction speaker\headphone (804) and a control unit (not shown).

In clinical trials carried out by the inventors of the present application it demonstrated that patients who were able to comfortably control the system following a brief, several minutes trial. As a non-limiting example provide below as Table 1, in a clinical trial held at Rambem Hospital, Israel, studying the "call for help" function required an average training time of 1.12 minutes, studying to communicate predetermined set of sentences required an average training time of 6.44 minutes, and free-text letter by letter communication using a mobile screen required an average training time of 11.08 minutes.

TABLE 1

| Communication type | Average training time (minutes) |
|---|---|
| "Call for help" | 1.12 |
| A sentence | 6.44 |
| Free text | 11.08 |

Figure 9:
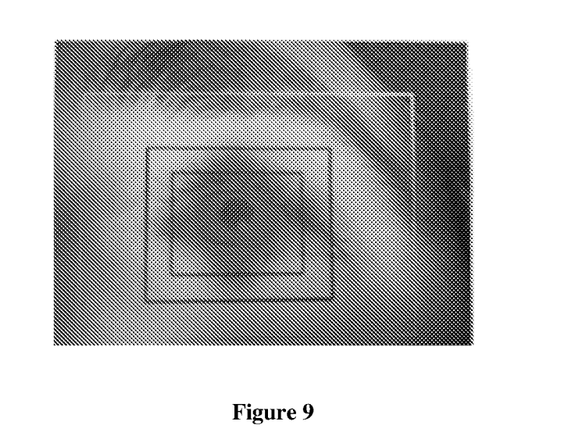
FIG. 9 is a schematic illustration of a one embodiment of the joystick-like gesture classification in which the position of the pupil area is determined based on a threshold map (the innermost square), a position map (the middle square) and the ROI map (the outmost square).
Figure 10:
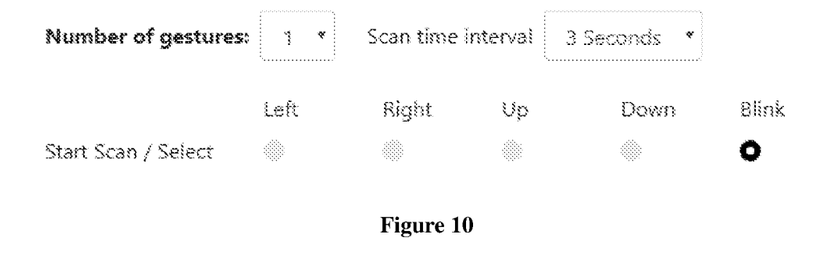
FIG. 10 is an illustration of one embodiment of mapping between an eye gesture and commands in a single gesture operation mode.
Figure 11:
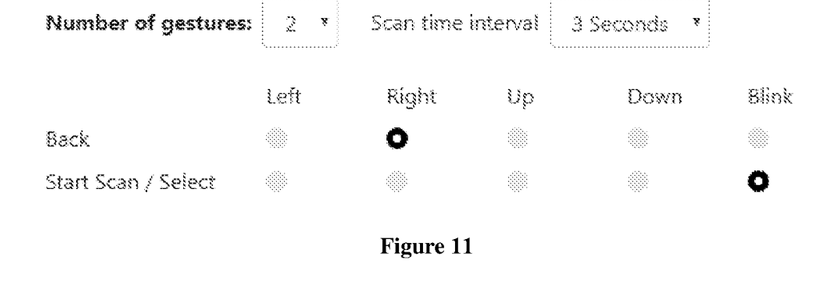
FIG. 11 is an illustration of one embodiment of mapping between eye gestures and commands in a two gestures operation mode.
Figure 12:
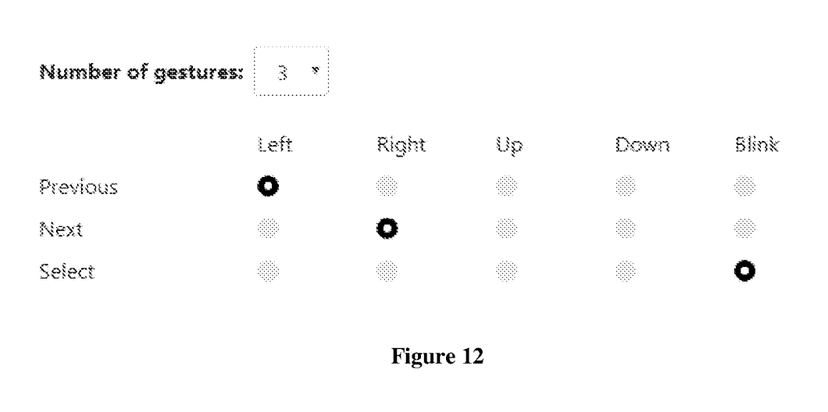
FIG. 12 is an illustration of one embodiment of mapping between eye gestures and commands in a three gestures operation mode.
Figure 13:
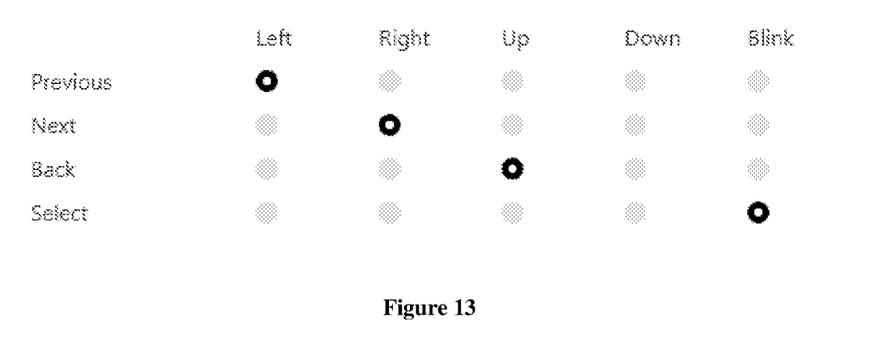
FIG. 13 is an illustration of one embodiment of mapping between eye gestures and commands in a four gestures operation mode.
Figure 14:
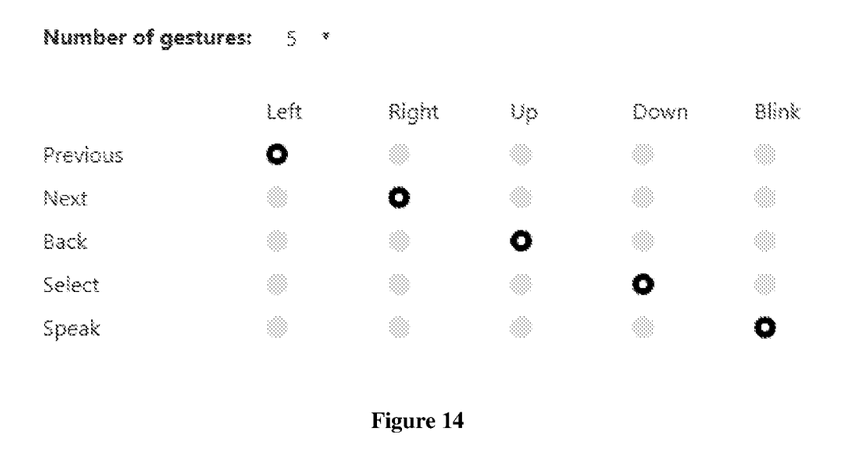
FIG. 14 is an illustration of one embodiment of mapping between eye gestures and commands in a five gestures operation mode.

A non-limiting embodiment of the joystick-like gesture classification is illustrated in FIG. 9. The classification is based on finding the position of the pupil area. It is obtained based on a threshold map (the innermost square). Specifically a particular position is determined whenever the pupil area touches a border or tangent to a border of the threshold map. For instance, when the pupil area touches the upper border of the threshold map the image data would be classified as an "up" gesture. The threshold map may be derived from a position map (the middle square), for instance being at least 80% away from the center of the position map, and optionally, the position map is within a larger, region of interest (ROI), defined based on anatomical features of the eye or its surrounding.

FIGS. 10-14 provides illustrations of several embodiments of mapping between eye gestures and commands in a single, two, three, four and five gestures operation modes. According to the mapping illustrated in FIG. 10 the user may initiate a scan session and select items by performing a blink gesture. According to the mapping illustrated in FIG. 11 the user may initiate a scan session and select items by performing a blink gesture, and selecting a back command by performing a "right" gesture. According to the mapping illustrated in FIG. 12 the user may traverse the menu items with two gestures ("right", and "left") and select items by performing a third, blink gesture. According to the mapping illustrated in FIG. 13 the user may traverse the menu items with three gestures ("right", "left", "up") and select items by performing a blink gesture. According to the mapping illustrated in FIG. 14 the user may traverse the menu items with four gestures ("right", "left", "up", "down") and select items by performing a blink gesture.

The invention claimed is:

1. An eye tracking-based system, comprising:
   a camera operable for continuously capturing images of one or both of the user's eye and eyelid and generating image data representative thereof;
   a first output module, a computerized or process-driven module; and a control unit in data communication with the camera and with the first output module;
   wherein the control unit is configured for
   receiving and processing said image data to identify at least one of pupil position and eyelid movement, and to classify the eye image into gestures based on pupil position and pupil presence duration within an area of a threshold map, said processing further comprises determining whenever the pupil area touches a border or is tangent to a border of the threshold map, to thereby define the gesture type, selected from one or more of pupil position, sequence of pupil positions, and sequences of eyelid blinks and generating gesture data,
   operating a hierarchical user-selectable menu items to permit the user to navigate through and select menu items by said gestures data, and for
   driving the first output module to present the menu items to the user;
   and wherein the first output module is configured for providing the user with audio presentation of a time-based prompt menu for selection of items with a predefined gesture, wherein a first menu item is announced in time $t_1$ and a second menu item is announced in $t_2$, and a third menu item is announced in $t_3$,
   the first menu item is selected if said predefined gesture is made in a time between $t_1$ and $t_2$ and the second menu item is selected if said predefined gesture is made in a time between $t_2$ and $t_3$.

2. The system of claim 1, wherein said camera is carried on a holder attachable to the user's head.

3. The system of claim 1, comprising a driver for a second output module for outputting data representative of selected items.

4. The system of claim 3, wherein the second output module is configured for outputting an alert.

5. The system of claim 4, wherein at least one gesture triggers said alert.

6. The system of claim 3, wherein the second output module is configured for outputting an alert to a care-giver.

7. An eye tracking-based system, comprising: a camera operable for continuously capturing images of one or both of the user's eye and eyelid and generating image data representative thereof;
   a first output module, a computerized or process-driven module; and a control unit in data communication with the camera and with the first output module;
   wherein the control unit is configured for
   receiving and processing said image data to identify at least one of pupil position and eyelid movement, and to classify these into gestures comprising one or more of pupil position, sequence of pupil positions, and sequences of eyelid blinks and generating gesture data,
   operating a hierarchical user-selectable menu items to permit the user to navigate through and select menu items by said gesture data, and for
   driving the first output module to present the menu items to the user;
   and wherein the first output module is configured for providing the user with audio presentation of a time-based prompt menu for selection of items with a predefined gesture, wherein a first menu item is announced in time $t_1$ and a second menu item is announced in $t_2$, and a third menu item is announced in $t_3$, the first menu item is selected if said predefined gesture is made in a time between $t_1$ and $t_2$ and the second menu item is selected if said predefined gesture is made in a time between $t_2$ and $t_3$.

8. An eye tracking-based system, comprising:
   a camera operable for continuously capturing images of one or both of the user's eye and eyelid and generating image data representative thereof;
   a first output module, a computerized or process-driven module; and a control unit in data communication with the camera and with the first output module;
   wherein the control unit is configured for
   receiving and processing said image data to identify at least one of pupil position and eyelid movement, and to classify the eye image into gestures based on pupil position and pupil presence duration within an area of a threshold map, said processing further comprises determining whenever the pupil area touches a border or is tangent to a border of the threshold map, to thereby define the gesture type, selected from one or more of pupil position, sequence of pupil positions, and sequences of eyelid blinks and generating gesture data,
   operating a hierarchical user-selectable menu items to permit the user to navigate through and select menu items by said gestures data, and for
   driving the first output module to present the menu items to the user;
   and wherein the first output module is configured for providing the user with audio presentation of a time-based prompt menu for selection of items with a predefined gesture, wherein a first menu item is announced in time $t_1$ and a second menu item is announced in $t_2$, and a third menu item is announced in $t_3$,
   wherein if said predefined gesture is made in a time t, the first menu item is selected if t is between $t_1$ and $t_2$ and the second menu item is selected if t is between $t_2$ and $t_3$.

9. An eye tracking-based system, comprising:
   a camera operable for continuously capturing images of one or both of the user's eye and eyelid and generating image data representative thereof;
   a first output module, a computerized or process-driven module; and a control unit in data communication with the camera and with the first output module;
   wherein the control unit is configured for
   receiving and processing said image data to identify at least one of pupil position and eyelid movement, and to classify the eye image into gestures based on pupil position and pupil presence duration within an area of a threshold map, said processing further comprises determining whenever the pupil area touches a border or is tangent to a border of the threshold map, to thereby define the gesture type, selected from one or more of pupil position, sequence of pupil positions, and sequences of eyelid blinks and generating gesture data,
   operating a hierarchical user-selectable menu items to permit the user to navigate through and select menu items by said gestures data, and for driving the first output module to present the menu items to the user;

and wherein the first output module is configured for providing the user with audio presentation of a time-based prompt menu for selection of items with a predefined gesture, wherein a first menu item is announced in time $t_1$ and a second menu item is announced in $t_2$, and a third menu item is announced in $t_3$, wherein $t_2$ is a time after $t_1$ and $t_3$ is a time after $t_2$, the first menu item is selected if said predefined gesture is made in a time frame between $t_1$ and $t_2$ and the second menu item is selected if said predefined gesture is made in a time frame between $t_2$ and $t_3$.

\* \* \* \* \*